(12) United States Patent
Zadina et al.

(10) Patent No.: US 8,716,436 B2
(45) Date of Patent: May 6, 2014

(54) MU OPIOID RECEPTOR AGONIST ANALOGS OF THE ENDOMORPHINS

(75) Inventors: James E. Zadina, Metairie, LA (US); Laszlo Hackler, Metairie, LA (US)

(73) Assignees: The Administrators of the Tulane Educational Fund, New Orleans, LA (US); U.S. Department of Veterans Affairs, Washington, DC (US)

( * ) Notice: Subject to any disclaimer, the term of this patent is extended or adjusted under 35 U.S.C. 154(b) by 0 days.

(21) Appl. No.: 13/477,423

(22) Filed: May 22, 2012

(65) Prior Publication Data

US 2012/0322740 A1    Dec. 20, 2012

Related U.S. Application Data

(63) Continuation-in-part of application No. PCT/US2011/043306, filed on Jul. 8, 2011.

(60) Provisional application No. 61/363,039, filed on Jul. 9, 2010.

(51) Int. Cl.
*C07K 5/02* (2006.01)
*C07K 7/00* (2006.01)
*C07K 7/50* (2006.01)
*C07K 7/54* (2006.01)
*C07K 7/56* (2006.01)
*C07K 5/03* (2006.01)

(52) U.S. Cl.
USPC ......... 530/317; 514/17.7; 514/18.3; 514/18.4

(58) Field of Classification Search
None
See application file for complete search history.

(56) References Cited

U.S. PATENT DOCUMENTS

| | | | |
|---|---|---|---|
| 5,872,097 A | | 2/1999 | Fhölenhag et al. |
| 5,885,958 A | * | 3/1999 | Zadina et al. ............... 514/18.4 |
| 6,303,578 B1 | | 10/2001 | Zadina et al. |
| 7,399,762 B2 | | 7/2008 | Carroll et al. |
| 2006/0105947 A1 | * | 5/2006 | Carr et al. ................. 514/12 |

OTHER PUBLICATIONS

Janecka et al., Synthesis and antinocicieptive activity of cyclic endomorphin-2 and morphiceptin analogs, Biochemical Pharmacology, 71(2005)188-195.*
Pakkala et al, "Activity and stability of human kallikrein-2-specific linear and cyclic peptide inhibitors," J. Pept. Sci. 2007: 13:348-353.*
Czapla M.A. et al., "Reduced Suppression of CO2-Induced Ventilatory Stimulation by Endomorphins Relative to Morphine", Brain Res., 1059 (2), 159-166 (2005).
Czapla M., et al., Differential Cardiorespiratory Effects of Endomorphin 1,Endomorphin 2, DAMGO, and Morphine, American Journal of Respiratory and Critical Care Medicine, vol. 162, 994-999 (2000).
Lenard, N.R. et al., Absence of Conditioned Place Preference or Reinstatement with Bivalent Ligands Containing Mu-Opioid Receptor Agonist and Delta-Opioid Receptor Antagonist Pharmacophores, Eur. J. Pharmacol, 566 (1-3), 75-82 (2007).
Wilson, A.M. et al., Dissociation of Analgesic and Rewarding Effects of Endomorphin-1 in Rats, Peptides, 21 (12), 1871-1874 (2000).
Zadina, J.E. et al., "A Potent and Selective Endogenous Agonist for the mu-Opiate Receptor", Nature 386 (6624), 499-502 (1997).
Purington, L.C. et al., Pentapeptides Displaying Mu Opioid Receptor Agonist and Delta Opioid Receptor Partial Agonist/Antagonist Properties, J. Med. Chem., 52 (23), 7724-7731 (2009).
R. Perlikowska, J.C. Do-Rego, A. Cravezic, J. Fichna, A. Wyrebska, G. Toth, A Janecka; Peptides 2010; 31;339-345.

* cited by examiner

*Primary Examiner* — Maury Audet
*Assistant Examiner* — Joseph Fischer
(74) *Attorney, Agent, or Firm* — Olson & Cepuritis, Ltd.

(57) ABSTRACT

The invention relates to cyclic peptide agonists that bind to the mu (morphine) opioid receptor and their use in the treatment of acute and/or chronic pain. Embodiments of the invention are directed to cyclic pentapeptide and hexapeptide analogs of endomorphin that have (i) a carboxy-terminal extension with an amidated hydrophilic amino acid and (ii) a substitution in amino acid position 2. These peptide analogs exhibit decreased tolerance relative to morphine, increased solubility compared to similar tetrapeptide analogs, while maintaining favorable or improved therapeutic ratios of analgesia to side effects.

8 Claims, 7 Drawing Sheets

Tyr-c[D-Lys-Trp-Phe-Glu]-NH$_2$
(SEQ ID NO:1)

C$_{40}$H$_{48}$N$_8$O$_7$

MW=752.3646

Tyr-c[D-Glu-Phe-Phe-Lys]-NH₂
(SEQ ID NO:2)

C₃₈H₄₇N₇O₇

MW=713.3535

Tyr-c[D-Glu-Phe-Phe-Lys]-Gly-NH$_2$
(SEQ ID NO:4)

C$_{40}$H$_{50}$N$_8$O$_8$

MW=770.3752

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: Cyclic endomorphin analog; residues 2-5 form a
      cyclic structure
<221> NAME/KEY: VARIANT
<222> LOCATION: 2
<223> OTHER INFORMATION: Xaa = D-Lys

<400> SEQUENCE: 1

Tyr Xaa Trp Phe Glu
 1               5

<210> SEQ ID NO 2
<211> LENGTH: 5
<212> TYPE: PRT
<213> ORGANISM: Artificial Sequence
<220> FEATURE:
<223> OTHER INFORMATION: Cyclic endomorphin analog; residues 2-5 form a
      cyclic structure
<221> NAME/KEY: VARIANT
<222> LOCATION: 2
<223> OTHER INFORMATION: Xaa = D-Glu

<400> SEQUENCE: 2

Tyr Xaa Phe Phe Lys
 1               5

<210> SEQ ID NO 3
<211> LENGTH: 6
<212> TYPE: PRT
<213> ORGANISM: Artificial Sequence
<220> FEATURE:
<223> OTHER INFORMATION: Cyclic endomorphin analog; residues 2-5 form a
      cyclic structure
<221> NAME/KEY: VARIANT
<222> LOCATION: 2
<223> OTHER INFORMATION: Xaa = D-Lys

<400> SEQUENCE: 3

Tyr Xaa Trp Phe Glu Gly
 1               5

<210> SEQ ID NO 4
<211> LENGTH: 6
<212> TYPE: PRT
<213> ORGANISM: Artificial Sequence
<220> FEATURE:
```

```
<223> OTHER INFORMATION: Cyclic endorphin analog; residues 2-5 form a
      cyclic structure
<221> NAME/KEY: VARIANT
<222> LOCATION: 2
<223> OTHER INFORMATION: Xaa = D-Glu

<400> SEQUENCE: 4

Tyr Xaa Phe Phe Lys Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Cyclic endorphin analog; residues 2-5 form a
      cyclic structure
<221> NAME/KEY: VARIANT
<222> LOCATION: 2
<223> OTHER INFORMATION: Xaa = D-Lys

<400> SEQUENCE: 5

Tyr Xaa Trp Phe Asp
1               5

<210> SEQ ID NO 6
<211> LENGTH: 5
<212> TYPE: PRT
<213> ORGANISM: Artificial Sequence
<220> FEATURE:
<223> OTHER INFORMATION: Cyclic endorphin analog; residues 2-5 form a
      cyclic structure
<221> NAME/KEY: VARIANT
<222> LOCATION: 2
<223> OTHER INFORMATION: Xaa = D-Glu
<221> NAME/KEY: VARIANT
<222> LOCATION: 4
<223> OTHER INFORMATION: Xaa = N-methyl-Phe

<400> SEQUENCE: 6

Tyr Xaa Phe Xaa Lys
1               5

<210> SEQ ID NO 7
<211> LENGTH: 6
<212> TYPE: PRT
<213> ORGANISM: Artificial Sequence
<220> FEATURE:
<223> OTHER INFORMATION: Cyclic endorphin analog; residues 2-5 form a
      cyclic structure
<221> NAME/KEY: VARIANT
<222> LOCATION: 2
<223> OTHER INFORMATION: Xaa = D-Orn
<221> NAME/KEY: VARIANT
<222> LOCATION: 4
<223> OTHER INFORMATION: Xaa = p-Cl-Phe

<400> SEQUENCE: 7

Tyr Xaa Phe Xaa Asp Val
1               5

<210> SEQ ID NO 8
<211> LENGTH: 4
<212> TYPE: PRT
<213> ORGANISM: Homo sapiens

<400> SEQUENCE: 8

Tyr Pro Trp Phe
1
```

```
<210> SEQ ID NO 9
<211> LENGTH: 4
<212> TYPE: PRT
<213> ORGANISM: Homo sapiens

<400> SEQUENCE: 9

Tyr Pro Phe Phe
 1

<210> SEQ ID NO 10
<211> LENGTH: 4
<212> TYPE: PRT
<213> ORGANISM: Artificial Sequence
<220> FEATURE:
<223> OTHER INFORMATION: Cyclic tetrapeptide; residues 2-4 form a cyclic
      structure
<221> NAME/KEY: VARIANT
<222> LOCATION: 2
<223> OTHER INFORMATION: Xaa = D-Lys

<400> SEQUENCE: 10

Tyr Xaa Trp Phe
 1

<210> SEQ ID NO 11
<211> LENGTH: 4
<212> TYPE: PRT
<213> ORGANISM: Artificial Sequence
<220> FEATURE:
<223> OTHER INFORMATION: Cyclic tetrapeptide; residues 2-4 form a cyclic
      structure
<221> NAME/KEY: VARIANT
<222> LOCATION: 2
<223> OTHER INFORMATION: Xaa = D-Lys

<400> SEQUENCE: 11

Tyr Xaa Phe Phe
 1
```

MU OPIOID RECEPTOR AGONIST ANALOGS OF THE ENDOMORPHINS

CROSS-REFERENCE TO RELATED APPLICATIONS

This application is a continuation-in-part of PCT/US2011/43306, filed on Jul. 8, 2011, which claims the benefit of U.S. Provisional Application Ser. No. 61/363,039, filed on Jul. 9, 2010, each of which is incorporated herein by reference in its entirety.

STATEMENT OF GOVERNMENT SUPPORT

A portion of the work described herein was supported by a Senior Career Research Scientist Award and Competitive Merit Review Program funding grant from the Department of Veteran Affairs to James E. Zadina. The United States government has certain rights in this invention.

FIELD OF THE INVENTION

The present invention relates to peptide agonists that bind to the mu (morphine) opioid receptor and their use in the treatment of acute and chronic pain.

BACKGROUND OF THE INVENTION

Activation of the mu opioid receptor is among the most effective means of alleviating a wide range of pain conditions. Of the recently cloned opioid receptors e.g., mu (3,20,21), delta (6,9), and kappa (12-14), the vast majority of clinically used opioids act at the mu receptor. As illustrated in genetically altered "knock-out" mice, the absence of the mu receptor eliminates the analgesic effects of morphine (8), illustrating its central role in opioid-induced pain relief. The unique effectiveness of mu agonists can be attributed to several factors, including their presence in numerous regions of the nervous system that regulate pain processing and activation of multiple mechanisms that limit pain transmission (e.g., inhibiting release of excitatory transmitters from the peripheral nervous system and decreasing cellular excitability in the central nervous system).

Limitations on the use of opioids result from negative side effects, including abuse liability, respiratory depression, and cognitive and motor impairment. Major efforts to develop compounds that maintain analgesic properties while reducing the negative side effects have met with limited success. This is evident from the recent epidemic of prescription drug abuse. Numerous attempts at targeting alternative mechanisms of pain relief to avoid these side effects have generally been met with similar problems, i.e., a profile of adverse effects that are different from opioids, but often sufficiently serious to warrant removal from the market (e.g., COX inhibitors) or lack of approval to enter the market (e.g., TRP receptor antagonists). Over 100 million patients annually in the United States experience acute or chronic pain and frequently do not achieve adequate relief from existing drugs due to limited efficacy or excessive side effects.

Elderly patients tend to show greater sensitivity to severe pain and recent guidelines of the American Geriatric Society suggest greater use of opioids and reduction of non-steroidal anti-inflammatory drugs (NSAIDs) (10). Impairment of motor and cognitive function can be more debilitating in the elderly than in younger patients, particularly due to increased risk of fractures (7). Opioids with reduced motor and cognitive impairment are therefore a growing unmet need.

Natural endogenous peptides from bovine and human brain that are highly selective for the mu opioid receptor relative to the delta or kappa receptor have been described (23 and U.S. Pat. No. 6,303,578 which is incorporated herein by reference in its entirety). These peptides are potent analgesics and have shown promise of reduced abuse liability (22) and respiratory depression (4,5), as measured in rodent studies. The limited metabolic stability of the natural peptides led to the development of cyclized, D-amino acid-containing tetrapeptide analogs of the endomorphins (U.S. Pat. No. 5,885,958 which is incorporated herein by reference in its entirety) of sufficient metabolic stability to produce potent analgesia in rodents after peripheral administration. A lead compound from this group reportedly was 3-fold more potent than morphine in alleviating neuropathic pain and showed reduced rewarding properties in animal models that are correlated with abuse potential. While these results are promising, the development of additional compounds showing equal or better properties is desirable. The instant invention addresses this need by providing peptide analogs having unexpectedly better solubility and side-effect profiles than the previously described materials.

SUMMARY OF THE INVENTION

An embodiment of the instant invention is directed to pentapeptide and hexapeptide analogs of endomorphins that differ from the previously described tetrapeptide analogs by having (i) a carboxy-terminal extension with an amidated hydrophilic amino acid, (ii) a substitution in amino acid position 2; or (iii) a combination of (i) and (ii). The pentapeptide and hexapeptide analogs of the present invention exhibit increased solubility relative to the tetrapeptides while maintaining favorable therapeutic ratios of analgesia-to-side effects.

The compounds of the present invention are cyclic peptides that act as mu opioid receptor agonists with high affinity. These compounds provide relief of acute pain, chronic pain, or both, and comprise or consist of compounds of Formula I: (I) H-Tyr-cyclo[$X_1$-$X_2$-$X_3$-$X_4$]-$X_5$. $X_1$ and $X_4$ each independently is an acidic amino acid (i.e., an amino acid comprising a carboxylic acid-substituted side-chain) or a basic amino acid (i.e., an amino acid comprising an amino-substituted side-chain), with the proviso that if $X_1$ is an acidic amino acid (e.g., D-Asp or D-Glu), then $X_4$ is a basic amino acid (e.g., Lys, Orn, Dpr, or Dab), and vice versa. Preferably, $X_1$ is D-Asp, D-Glu, D-Lys, D-Orn, D-Dpr or D-Dab; while $X_4$ preferably is Asp, Glu, Lys, Orn, Dpr or Dab. $X_2$ and $X_3$ each independently is an aromatic amino acid (i.e., an amino acid comprising an aromatic group in the side chain thereof). For example, $X_2$ preferably is Trp, Phe, or N-alkyl-Phe, where the alkyl group preferably comprises 1 to about 6 carbon atoms, i.e., a ($C_1$ to $C_6$) alkyl group. $X_3$ preferably is Phe, D-Phe, or p-Y-Phe where Y is $NO_2$, F, Cl, or Br. $X_5$ is selected from the group consisting of —NHR, Ala-NHR, Arg-NHR, Asn-NHR, Asp-NHR, Cys-NHR, Glu-NHR, Gln-NHR, Gly-NHR, His-NHR, Ile-NHR, Leu-NHR, Met-NHR, Orn-NHR, Phe-NHR, Pro-NHR, Ser-NHR, Thr-NHR, Trp-NHR, Tyr-NHR, and Val-NHR; where R is H or an alkyl group (e.g. a ($C_1$ to $C_{10}$) alkyl group such as methyl, ethyl, propyl, isopropyl, butyl, isobutyl, pentyl, isopentyl, hexyl, isohexyl, heptyl, or isoheptyl). The peptide of Formula I is cyclic (shown as "c[$X_1$-$X_2$-$X_3$-$X_4$]" or "cyclo[$X_1$-$X_2$-$X_3$-$X_4$]" in the formulas described herein) by virtue of an amide linkage between the carboxylic acid and amino substituents of the side chains of amino acid residues $X_1$ and $X_4$. For example, the linkage can be an amide bond formed between the side chain amino group of the D-Lys, D-Orn, D-Dpr, D-Dab, Lys, Orn, Dpr, or Dab with the side chain carboxyl group of D-Asp, D-Glu, Asp, or Glu.

In one embodiment of the invention directed to a peptide of Formula I, $X_5$ is NHR, R is H, and $X_5$ can be —$NH_2$ (i.e., the peptide is an amidated pentapeptide), or Ala-$NH_2$, Arg-$NH_2$, Asn-$NH_2$, Asp-$NH_2$, Cys-$NH_2$, Glu-$NH_2$, Gln-$NH_2$, Gly-$NH_2$, His-$NH_2$, Ile-$NH_2$, Leu-$NH_2$, Met-$NH_2$, Orn-$NH_2$, Phe-$NH_2$, Pro-$NH_2$, Ser-$NH_2$, Thr-$NH_2$, Trp-$NH_2$, Tyr-$NH_2$, or Val-$NH_2$, (i.e., the peptide is an amidated hexapeptide). In one particular embodiment, $X_5$ is $NH_2$. In other particular embodiments, $X_5$ is Ala-$NH_2$, Arg-$NH_2$, Asn-$NH_2$, Asp-$NH_2$, Cys-$NH_2$, Glu-$NH_2$, Gln-$NH_2$, Gly-$NH_2$, His-$NH_2$, Ile-$NH_2$, Leu-$NH_2$, Met-$NH_2$, Orn-$NH_2$, Phe-$NH_2$, Pro-$NH_2$, Ser-$NH_2$, Thr-$NH_2$, Trp-$NH_2$, Tyr-$NH_2$, or Val-$NH_2$.

Another embodiment of the invention is directed to a peptide of Formula I, wherein $X_1$ is D-Asp, D-Glu, D-Lys, or D-Orn; and $X_4$ is Asp, Glu, Lys, or Orn.

Another embodiment of the invention is directed to a compound of Formula I, wherein $X_5$ is NHR and R is a ($C_1$ to $C_{10}$) alkyl.

Another embodiment of the invention is directed to a peptide of Formula I, wherein the aromatic amino acid of $X_2$ is Trp, Phe, or N-alkyl-Phe, and the alkyl group of N-alkyl-Phe is a ($C_1$ to $C_6$) alkyl. In one particular embodiment, $X_2$ is N-methyl-Phe (N-Me-Phe).

Another embodiment of the invention is directed to a peptide of Formula I, wherein the aromatic amino acid residue of either $X_2$ or $X_3$ is Phe, D-Phe, Trp, D-Trp, D-Tyr, N-alkyl-Phe, and the alkyl group of N-alkyl-Phe is ($C_1$ to $C_{10}$) alkyl or p-Y-Phe, wherein Y is $NO_2$, F, Cl, or Br.

Another embodiment of the invention is directed to a peptide of Formula I, wherein the aromatic amino acid of $X_3$ is Phe, D-Phe, or p-Y-Phe, wherein Y is $NO_2$, F, Cl, or Br. In one particular embodiment, $X_3$ is p-Cl-Phe.

Another embodiment of the invention is directed to a peptide of Formula I selected from the group consisting of Tyr-c[D-Lys-Trp-Phe-Glu]-$NH_2$ (SEQ ID NO:1); Tyr-c[D-Glu-Phe-Phe-Lys]-$NH_2$ (SEQ ID NO:2); Tyr-c[D-Lys-Trp-Phe-Glu]-Gly-$NH_2$ (SEQ ID NO:3); Tyr-c[D-Glu-Phe-Phe-Lys]-Gly-$NH_2$ (SEQ ID NO:4); Tyr-c[D-Lys-Trp-Phe-Asp]-$NH_2$ (SEQ ID NO:5); Tyr-c[D-Glu-N-Me-Phe-Phe-Lys]-$NH_2$ (SEQ ID NO:6); and Tyr-c[D-Orn-Phe-p-Cl-Phe-Asp]-Val-$NH_2$ (SEQ ID NO:7). The biological sequence information in this application is included in an ASCII text file having the file name "TU386CIPSEQ.txt", created on Aug. 24, 2012, and having a file size of 3,011 bytes, which is incorporated herein by reference.

Another aspect of the invention is directed to a pharmaceutical composition comprising a peptide of Formula I and a pharmaceutically acceptable carrier (e.g., a diluent or excipient).

Yet another aspect of the invention is directed to the use of a peptide of Formula I in a method of treating a patient having a condition that responds to an opioid, or a condition for which opioid treatment is standard in the art. Such a method comprises or consists of administering to the patient an effective amount of a peptide of Formula I of the invention. Particular embodiments of this method can be followed for the purpose of providing at least one effect selected from (i) analgesia (pain relief), (ii) relief from a gastrointestinal disorder such as diarrhea, (iii) therapy for an opioid drug dependence, and (iv) treatment of any condition for which an opioid is indicated. In some embodiments the peptides of Formula I can be used to treat acute or chronic pain. Uses for the peptides of Formula I also include, but are not limited to, use as antimigraine agents, immunomodulatory agents, immunosuppressive agents or antiarthritic agents. Certain embodiments of the methods of the present invention, such as treatment of pain or opioid drug dependence, are directed to patients having a history of opioid substance abuse. In certain embodiments of the present methods, the peptide is administered parenterally (e.g., intravenous). This invention also relates to a peptide of Formula I for use in one of said methods of treatment.

Another aspect of the invention is directed to a method of activating or regulating a mu-opioid receptor by contacting the mu-opioid receptor with a compound of the invention, as well as the use of the peptide of Formula I in such a treatment.

Another aspect of the invention is directed to a method of measuring the quantity of a mu opioid receptor in a sample using a peptide of Formula I. This method can comprise or consist of the following steps: (i) contacting a sample suspected of containing a mu opioid receptor with a peptide of Formula I to form a compound-receptor complex, (ii) detecting the complex, and (iii) quantifying the amount of complex formed.

Another aspect of the invention is directed to the use of a peptide of Formula I to perform a competitive assay method of detecting the presence of a molecule that binds to a mu opioid receptor. This method can comprise or consist of the following steps: (i) contacting a sample suspected of containing a molecule that binds to a mu opioid receptor with a mu opioid receptor and a peptide of Formula I, wherein the compound and receptor form a compound-receptor complex; (ii) measuring the amount of the complex formed in step (i); and (iii) comparing the amount of complex measured in step (ii) with the amount of a complex formed between the mu opioid receptor and the peptide in the absence of said sample.

portion of the peptide is formed from amino acid residues 2 through 4, while the Tyr residue (residue 1) is attached to residue 2 as a branch. Non-limiting examples of peptides with the composition of Formula I include Compounds 1-7 below, wherein the side chains of amino acid residues 2 ($X_1$) and 5 ($X_4$) in the sequence are linked by an amide bond between the side-chains thereof. The formulae of Compounds 1, 2, 3, 4, 5, 6, and 7 are shown in Table 1.

TABLE 1

| Compound | H-Tyr- | $X_1$- | $X_2$- | $X_3$- | $X_4$- | $X_5$ | SEQ ID NO: |
|---|---|---|---|---|---|---|---|
| 1 | Tyr- | c[D-Lys | Trp | Phe | Glu] | $NH_2$ | (SEQ ID NO: 1) |
| 2 | Tyr- | c[D-Glu | Phe | Phe | Lys] | $NH_2$ | (SEQ ID NO: 2) |
| 3 | Tyr- | c[D-Lys | Trp | Phe | Glu] | Gly-$NH_2$ | (SEQ ID NO: 3) |
| 4 | Tyr- | c[D-Glu | Phe | Phe | Lys] | Gly-$NH_2$ | (SEQ ID NO: 4) |
| 5 | Tyr- | c[D-Lys | Trp | Phe | Asp] | $NH_2$ | (SEQ ID NO: 5) |
| 6 | Tyr- | c[D-Glu | N-Me-Phe | Phe | Lys] | $NH_2$ | (SEQ ID NO: 6) |
| 7 | Tyr- | c[D-Orn | Phe | p-Cl-Phe | Asp] | Val-$NH_2$ | (SEQ ID NO: 7) |

*p<0.05. (B) The cumulative doses of either morphine or Compound 1 that were shown to produce maximal antinociception as shown in (A) were tested for the ability to induce conditioned place preference (CPP). ***p<0.01.

Figure 8:
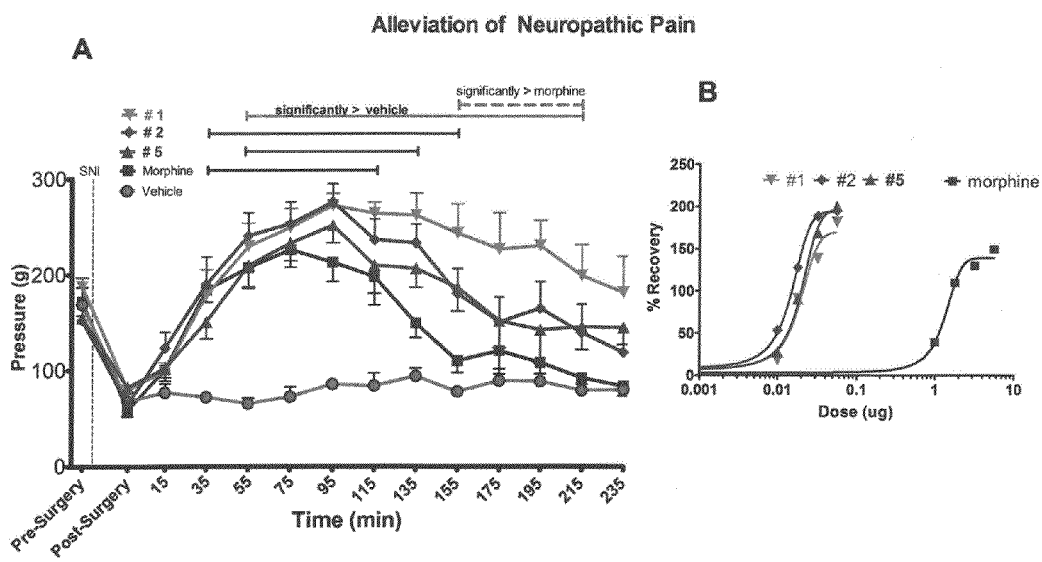

FIG. 8 shows the duration and relative potency of compounds in reversing chronic pain induced by nerve injury (neuropathic pain). (A) The decrease in paw pressure required for withdrawal after nerve injury surgery was reversed by morphine and Compounds 1, 2, and 5 (squares, down triangles, diamonds, and up triangles, respectively). Times at which the reversal was significantly above vehicle (p<0.05 to 0.001) are shown in bars at the top. Scores for Compound 1 were also significantly above those of morphine from 155 to 215 min (dashed bar). Compound 5 showed similar reversal (80 min) relative to morphine, and Compounds 1 and 2 showed significantly longer reversal (120 and 260 min, respectively) relative to morphine. (B) Dose-response curves show that all three analogs are significantly more potent than morphine, as determined by the dose required to fully (100%) reverse hyperalgesia (pre-surgical minus post-surgical pressure).

Figure 9:
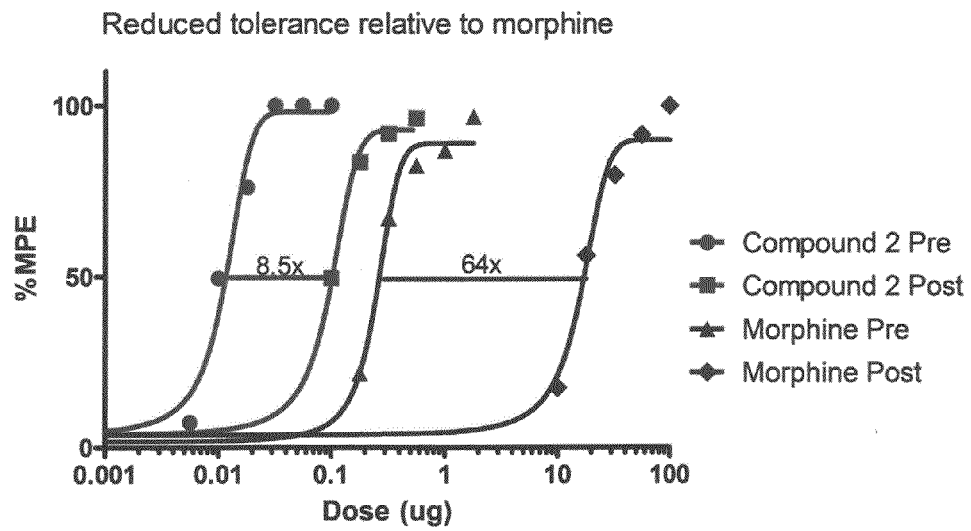

FIG. 9 shows the extent of tolerance produced by intrathecal delivery of morphine or Compound 2 for 1 week via an osmotic minipump. Cumulative dose-response curves (four increasing quarter-log doses) were used and responses expressed as % maximum possible effect (% MPE) in a tail-flick test were determined before and after implantation of a minipump. The shift in $ED_{50}$ after Compound 2 (about 8.5-fold) was significantly less than that after morphine (64 fold), consistent with reduced induction of tolerance by the analog. Similar results were observed with Compounds 1 and 5.

Figure 10:
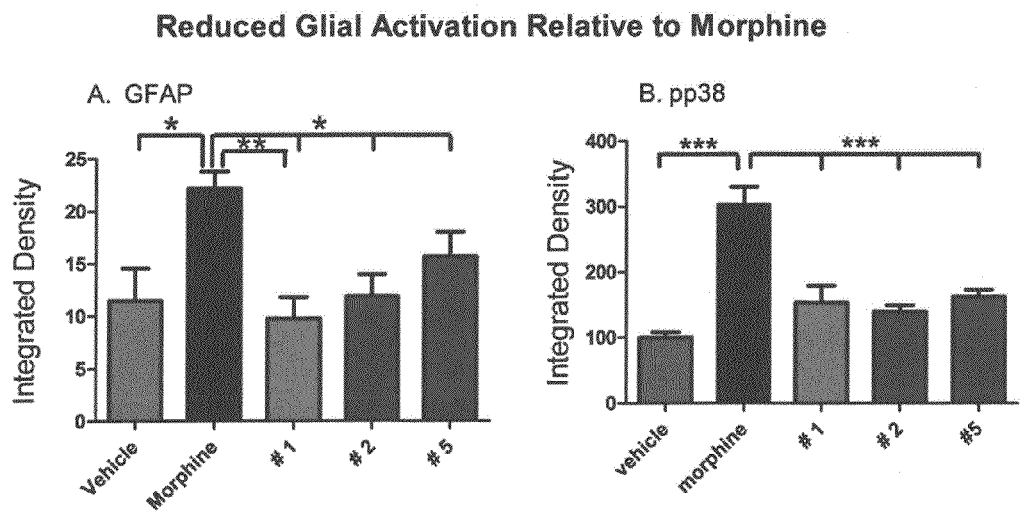

FIG. 10 shows activation of glia after 1 week of treatment with morphine but not analogs. Integrated density of GFAP (A) and pp38 (B) staining in morphine-treated, but not analog-treated rats is significantly increased relative to those given vehicle. In addition, the density of staining after morphine is significantly greater than that after analogs (*, , *=p<0.05, 0.01, 0.001,respectively; n=5-7).

DETAILED DESCRIPTION OF THE INVENTION

Peptides of Formula I, which are cyclic pentapeptide and hexapeptide analogs of endomorphin-1 (Tyr-Pro-Trp-Phe-$NH_2$, SEQ ID NO:8) and endomorphin-2 (Tyr-Pro-Phe-Phe-$NH_2$, SEQ ID NO:9) were prepared. In each case, the cyclic In some embodiments, the peptides of Formula I includes peptides with an N-alkylated phenylalanine in position 3 ($X_2$). Alkyl groups suitable in the peptides of the present invention include ($C_1$ to $C_{10}$) alkyl groups, preferably ($C_1$ to $C_6$) alkyl groups (e.g., methyl or ethyl). Compound 6 illustrates a cyclic analog whose linear primary amino acid sequence contains an N-methylated phenylalanine in position 3. Other peptides of this invention include compounds wherein the amino acid at position 4 ($X_3$) is p-Y-phenylalanine, wherein Y is $NO_2$, F, Cl or Br, in order to enhance receptor binding and potency. An exemplary peptide (Compound 7), whose linear primary amino acid sequence is provided in SEQ ID NO:7, has a p-chlorophenylalanine (p-Cl-Phe) in position 4.

Figure 1:
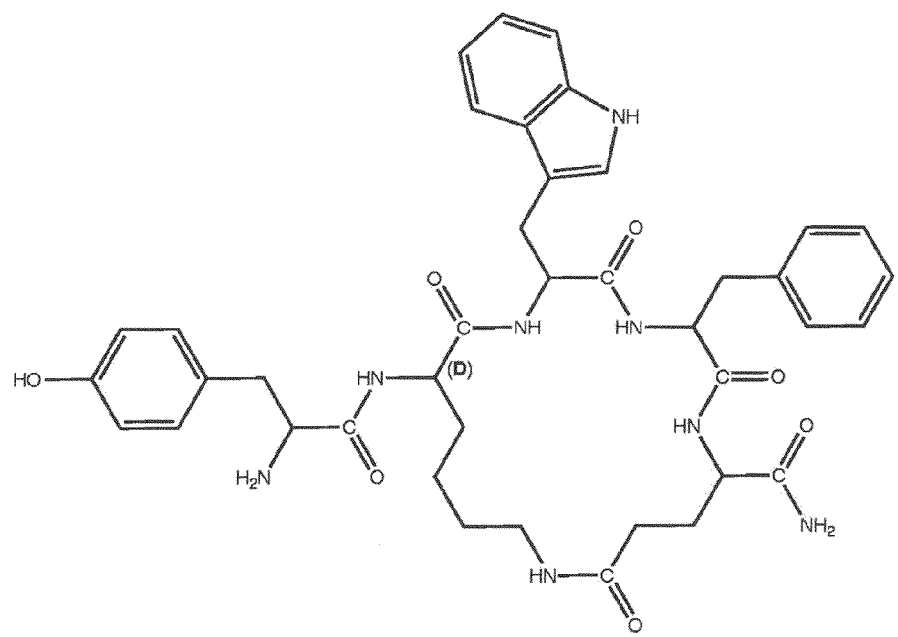
FIG. 1 shows Tyr-c[D-Lys-Trp-Phe-Glu]-$NH_2$ (SEQ ID NO:1), which is described as "Compound 1" in the following disclosure. The structural and basic molecular formulae, as well as the molecular weight (MW), are shown for Compound 1.
Figure 2:
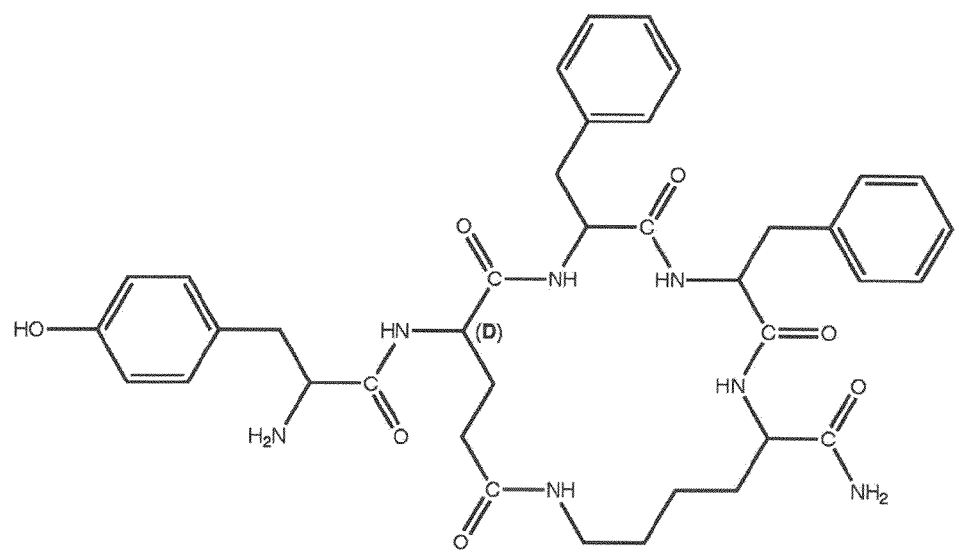
FIG. 2 shows Tyr-c[D-Glu-Phe-Phe-Lys]-$NH_2$ (SEQ ID NO:2), which is described as "Compound 2" in the following disclosure. The structural and basic molecular formulae, as well as the molecular weight (MW), are shown for Compound 2.
Figure 3:
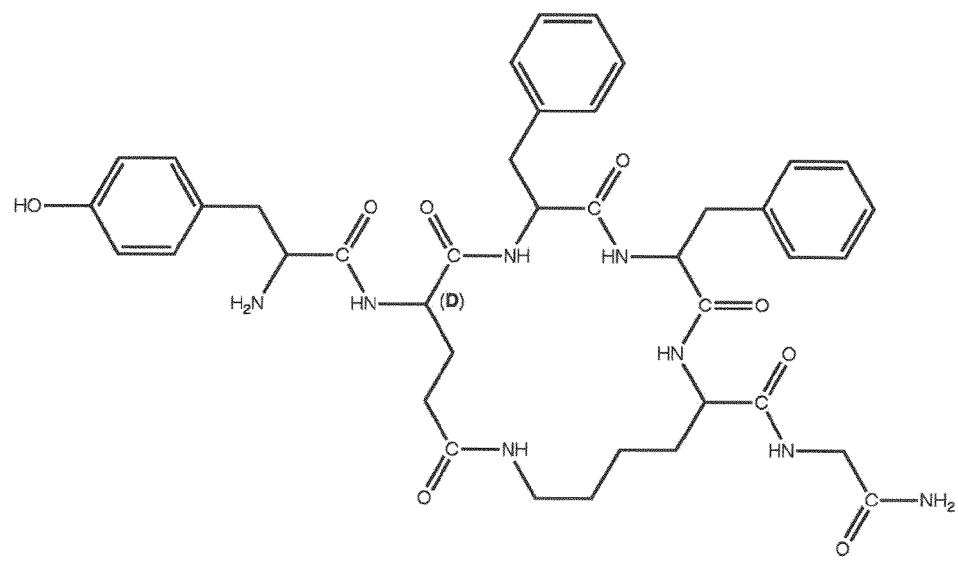
FIG. 3 shows Tyr-c[D-Glu-Phe-Phe-Lys]-Gly-$NH_2$ (SEQ ID NO:4), which is described as "Compound 4" in the following disclosure. The structural and basic molecular formulae, as well as the molecular weight (MW), are shown for Compound 4.

Compounds 1 (FIG. 1), 2 (FIGS. 2), 5 and 6 are examples of cyclic pentapeptides, and Compounds 3, 4 (FIGS. 3) and 7 are examples of cyclic hexapeptides of the instant invention.

For reference, the abbreviations for amino acids described herein include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), valine (Val), ornithine (Orn), naphthylalanine (Nal), 2,3-diaminopropionic acid (Dpr), and 2,4-diaminobutyric acid (Dab). The L- or D-enantiomeric forms of these and other amino acids can be included in the peptides of Formula I. Other amino acids, or derivatives or unnatural forms thereof such as those listed in the 2009/2010 Aldrich Handbook of Fine Chemicals (incorporated herein by reference in its entirety, particularly those sections therein listing amino acid derivatives and unnatural amino acids) can be used in preparing compounds of the invention.

In Formula I, $X_1$ can be, for example, D-Asp, D-Glu, D-Lys, D-Orn, D-Dpr or D-Dab, and $X_4$ can be, for example, Asp, Glu, Lys, Orn, Dpr or Dab. In general, an amino acid or derivative thereof can be used as $X_1$ or $X_4$ if it contains either an amino group or a carboxyl group in its side chain. In some embodiments, the amino acid used for $X_1$ can be a D-enantiomeric form of such amino acid.

$X_2$ and $X_3$ in Formula I are aromatic amino acids. Examples of such amino acids are unsubstituted or substituted aromatic amino acids selected from the group consisting of phenylalanine, heteroarylalanine, naphthylalanine (Nal), homophenylalanine, histidine, tryptophan, tyrosine, arylglycine, heteroarylglycine, thyroxine, aryl-beta-alanine, and heteroaryl-beta-alanine Examples of substituted versions of these aromatic amino acids are disclosed in U.S. Pat. No. 7,629,319, which is herein incorporated by reference in its entirety. As used herein, "aromatic amino acid" refers to an a-amino acid comprising an aromatic group (including aromatic hydrocarbon and aromatic heterocyclic groups) in the side-chain thereof.

In some embodiments, $X_2$ in Formula I can be N-alkyl-Phe, where the alkyl group comprises 1 to about 6 carbon atoms. Alternatively, the alkyl group can comprise about 1, 2, 3, 4, 5, 6, 7, 8, 9, or 10 carbons, for example. The alkyl group can be a methyl (i.e., $X_2$ is N-Me-Phe), ethyl, propyl, isopropyl, butyl, isobutyl, pentyl, isopentyl, hexyl, isohexyl, heptyl, or isoheptyl group, or any other branched form thereof, for example. By definition, the alkyl group of N-alkyl-Phe is linked to the a-amino group of phenylalanine This alpha amino group is involved in an amide bond with the $X_i$ residue in certain peptides of the invention; therefore, the alpha amino group of $X_2$ (when N-alkyl-Phe) as it exists in such peptides is a tertiary amide.

In some embodiments $X_3$ in Formula I is para-Y-Phe (p-Y-Phe), where Y is $NO_2$, F, Cl, or Br, for example. For example, $X_3$ can be p-Cl-Phe. Alternatively, the $NO_2$, F, Cl, or Br groups can be linked in the ortho or meta positions of the phenyl ring of Phe. Any aromatic amino acid incorporated in the compounds of the invention such as at $X_2$ or $X_3$ can have the above groups linked thereto in the ortho, meta, or para positions.

Solubility.

The solubility of the peptides of Formula I (e.g., in saline or physiologic buffer) typically is enhanced relative to the prior art tetrapeptide analogs of the endomorphins Addition of a hydrophilic amino acid and amidated C-terminus to the relatively hydrophobic tetrapeptide sequences Tyr-cyclo[D-Lys-Trp-Phe] (SEQ ID NO:10) and Tyr-cyclo[D-Lys-Phe-Phe] (SEQ ID NO:11), resulted in an unexpectedly high improvement in solubility while maintaining or improving functionality. For example, Compound 1 was soluble in water, saline and 20% PEG/saline at about 43, 21 and 90 mg/mL, respectively, compared to less than about 2 mg/mL for the previously described compounds. While increases in solubility are associated with improved pharmaceutical delivery properties, higher solubility is also often associated with reduced functional activity (e.g., receptor binding) that may depend on lipophilicity. Surprisingly however, as described in examples below, the functional properties of the compounds of the invention are not diminished, and indeed are generally improved.

Methods of Preparation of the Peptides of Formula I.

The peptides of Formula I can be prepared by conventional solution phase (2) or solid phase (18) methods with the use of proper protecting groups and coupling agents; references 2 and 20 are herein incorporated by reference in their entirety. Such methods generally utilize various protecting groups on the various amino acid residues of the peptides. A suitable deprotection method is employed to remove specified or all of the protecting groups, including splitting off the resin if solid phase synthesis is applied. The peptides can be synthesized, for example, as described below.

Peptides of Formula I were synthesized on Rink Amide resin via Fmoc chemistry. A t-butyl group was used for Tyr, Glu, Asp side chain protection and Boc was used for Lys, Orn and Trp side chain protection. All materials were obtained from EMD Biosciences, Inc (San Diego, Calif.). The peptide was assembled on Rink Amide resin by repetitive removal of the Fmoc protecting group and coupling of protected amino acid. HBTU (O-benzotriazole-N,N,N',N'-tetramethyluronium hexafluorophosphate; CAS #94790-37-1) and HOBT (N-hydroxybenzotriazole; CAS #2592-95-2) were used as coupling reagents in N,N-dimethylformamide (DMF) and diisopropylethylamine (DIPEA) was used as a base. The resin was treated with an aqueous cocktail of trifluoroacetic acid and triisopropylsilane (TFA/TIS/$H_2O$ cocktail) for cleavage and removal of the side chain protecting groups. Crude peptide was precipitated with diethyl ether and collected by filtration.

Cyclization of the linear Fmoc-Tyr-c[$X_1$-$X_2$-$X_3$-$X_4$]-$X_5$ precursors: About 1 mmol of peptide was dissolved in about 1000 mL DMF and about 2 mmol DIPEA was added to the solution, followed by a solution of HBTU (about 1.1 mmol) and HOBT (about 1.1 mmol) in about 100 mL DMF. The reaction mixture was stirred at room temperature overnight. Solvent was removed in vacuo. The resulting solid residue was washed with 5% citric acid, saturated NaCl, saturated $NaHCO_3$, and water. The final solid was washed with diethyl ether and dried under high vacuum.

Preparation of Tyr-c[$X_1$-$X_2$-$X_3$-$X_4$]-$X_5$ peptides. The solids obtained above were dissolved in 20% piperidine/DMF. The mixture was stirred at room temperature for about 1 hour. Solvent was removed in vacuo. Residues were dissolved in 10% aqueous acetonitrile (MeCN/$H_2O$) and lyophilized.

Purification of the crude lyophilized peptides was performed with reverse phase high performance liquid chromatography (RP-HPLC). The HPLC system GOLD 32 KARAT (Beckman) consisting of the programmable solvent module 126 and the diode array detector module 168 was used in the purification and the purity control of the peptides. Reverse phase HPLC was performed using a gradient made from two solvents: (A) 0.1% TFA in water and (B) 0.1% TFA in acetonitrile. For preparative runs, a VYDAC 218TP510 column (250×10 mm; Alltech Associates, Inc.) was used with a gradient of 5-20% solvent B in solvent A over a period of 10 min, 20-25% B over a period of 30 minutes, 25-80% B over a period of 1 minute and isocratic elution over 9 minutes at a flow rate of about 4 mL/min, absorptions being measured at both 214 and 280 nm. The same gradient was used for analytical runs on a VYDAC 218TP54 column (250×4.6 mm) at a flow rate of about 1 mL/min.

Pharmaceutical Preparations.

The instant invention also provides pharmaceutical preparations which contain a pharmaceutically effective amount of the peptides in a pharmaceutically acceptable carrier (e.g., a diluent, complexing agent, additive, excipient, adjuvant and the like). The peptide can be present for example in a salt form, a micro-crystal form, a nano-crystal form, a co-crystal form, a nanoparticle form, a mirocparticle form, or an amphiphilic form. The carrier can be an organic or inorganic carrier that is suitable for external, enteral or parenteral applications. The peptides of the present invention can be compounded, for example, with the usual non-toxic, pharmaceutically acceptable carriers for tablets, pellets, capsules, liposomes, suppositories, intranasal sprays, solutions, emulsions, suspensions, aerosols, targeted chemical delivery systems (15), and any other form suitable for use. Non-limiting examples of carriers that can be used include water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, liquid or aerosol form. In addition auxiliary, stabilizing, thickening and coloring agents and perfumes can be used. The present invention also provides pharmaceutical compositions useful for treating pain and related conditions, as described herein. The pharmaceutical compositions comprise at least one peptide of Formula I in combination with a pharmaceutically acceptable carrier, vehicle, or diluent, such as an aqueous buffer at a physiologically acceptable pH (e.g., pH 7 to 8.5), a polymer-based nanoparticle vehicle, a liposome, and the like. The pharmaceutical compositions can be delivered in any suitable dosage form, such as a liquid, gel, solid, cream, or paste dosage form. In one embodiment, the compositions can be adapted to give sustained release of the peptide.

In some embodiments, the pharmaceutical compositions include, but are not limited to, those forms suitable for oral, rectal, nasal, topical, (including buccal and sublingual), transdermal, vaginal, parenteral (including intramuscular, subcutaneous, and intravenous), spinal (epidural, intrathecal), and central (intracerebroventricular) administration. The compositions can, where appropriate, be conveniently provided in discrete dosage units. The pharmaceutical compositions of the invention can be prepared by any of the methods well known in the pharmaceutical arts. Some preferred modes of administration include intravenous (iv), topical, subcutaneous, oral and spinal.

Pharmaceutical formulations suitable for oral administration include capsules, cachets, or tablets, each containing a predetermined amount of one or more of the peptides, as a powder or granules. In another embodiment, the oral composition is a solution, a suspension, or an emulsion. Alternatively, the peptides can be provided as a bolus, electuary, or paste. Tablets and capsules for oral administration can contain conventional excipients such as binding agents, fillers, lubricants, disintegrants, colorants, flavoring agents, preservatives, or wetting agents. The tablets can be coated according to methods well known in the art, if desired. Oral liquid preparations include, for example, aqueous or oily suspensions, solutions, emulsions, syrups, or elixirs. Alternatively, the compositions can be provided as a dry product for constitution with water or another suitable vehicle before use. Such liquid preparations can contain conventional additives such as suspending agents, emulsifying agents, non-aqueous vehicles (which may include edible oils), preservatives, and the like. The additives, excipients, and the like typically will be included in the compositions for oral administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Pharmaceutical compositions for parenteral, spinal, or central administration (e.g. by bolus injection or continuous infusion) or injection into amniotic fluid can be provided in unit dose form in ampoules, pre-filled syringes, small volume infusion, or in multi-dose containers, and preferably include an added preservative. The compositions for parenteral administration can be suspensions, solutions, or emulsions, and can contain excipients such as suspending agents, stabilizing agents, and dispersing agents. Alternatively, the peptides can be provided in powder form, obtained by aseptic isolation of sterile solid or by lyophilization from solution, for constitution with a suitable vehicle, e.g. sterile, pyrogen-free water, before use. The additives, excipients, and the like typically will be included in the compositions for parenteral administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 100 millimolar, preferably at least about 1 nanomolar to about 10 millimolar.

Pharmaceutical compositions for topical administration of the peptides to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like. The additives, excipients, and the like typically will be included in the compositions for topical administration to the epidermis within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Pharmaceutical compositions suitable for topical administration in the mouth (e.g., buccal or sublingual administration) include lozenges comprising the peptide in a flavored base, such as sucrose, acacia, or tragacanth; pastilles comprising the peptide in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired. The additives, excipients, and the like typically will be included in the compositions of topical oral administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

A pharmaceutical composition suitable for rectal administration comprises a peptide of the present invention in combination with a solid or semisolid (e.g., cream or paste) carrier or vehicle. For example, such rectal compositions can be provided as unit dose suppositories. Suitable carriers or vehicles include cocoa butter and other materials commonly used in the art. The additives, excipients, and the like typically will be included in the compositions of rectal administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

According to one embodiment, pharmaceutical compositions of the present invention suitable for vaginal administration are provided as pessaries, tampons, creams, gels, pastes, foams, or sprays containing a peptide of the invention in combination with carriers as are known in the art. Alternatively, compositions suitable for vaginal administration can be delivered in a liquid or solid dosage form. The additives, excipients, and the like typically will be included in the compositions of vaginal administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Pharmaceutical compositions suitable for intra-nasal administration are also encompassed by the present invention. Such intra-nasal compositions comprise a peptide of the invention in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the peptide. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the peptide. Alternatively, pharmaceutical compositions for administration by inhalation or insufflation can be provided in the form of a dry powder composition, for example, a powder mix of the peptide and a suitable powder base such as lactose or starch. Such powder composition can be provided in unit dosage form, for example, in capsules, cartridges, gelatin packs, or blister packs, from which the powder can be administered with the aid of an inhalator or insufflator. The additives, excipients, and the like typically will be included in the compositions of intra-nasal administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Optionally, the pharmaceutical compositions of the present invention can include one or more other therapeutic agent, e.g., as a combination therapy. The additional therapeutic agent will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with a peptide of the present invention.

In another aspect, the present invention provides for the use of the peptides of Formula I for treatment of pain, treatment of discomfort associated with gastrointestinal disorders, and treatment of drug dependence. Methods for providing analgesia (alleviating or reducing pain), relief from gastrointestinal disorders such as diarrhea, and therapy for drug dependence in patients, such as mammals, including humans, comprise administering to a patient suffering from one of the aforementioned conditions an effective amount of a peptide of Formula I. Diarrhea may be caused by a number of sources, such as infectious disease, cholera, or an effect or side-effect of various drugs or therapies, including those used for cancer therapy. Preferably, the peptide is administered parenterally or enterally. The dosage of the effective amount of the peptides can vary depending upon the age and condition of each individual patient to be treated. However, suitable unit dosages typically range from about 0.01 to about 100 mg. For example, a unit dose can be in the range of about 0.2 mg to about 50 mg. Such a unit dose can be administered more than once a day, e.g., two or three times a day.

All of the embodiments of the peptides of Formula I can be in the "isolated" state. For example, an "isolated" peptide is one that has been completely or partially purified. In some instances, the isolated compound will be part of a greater composition, buffer system or reagent mix. In other circumstances, the isolated peptide may be purified to homogeneity. A composition may comprise the peptide or compound at a level of at least about 50, 80, 90, or 95% (on a molar basis or weight basis) of all the other species that are also present therein. Mixtures of the peptides of Formula I may be used in practicing methods provided by the invention.

Additional embodiments of the current invention are directed towards methods of using the peptides of Formula I disclosed herein in medicinal formulations or as therapeutic agents, for example. These methods may involve the use of a single peptide, or multiple peptides in combination (i.e., a mixture). Accordingly, certain embodiments of the invention are drawn to medicaments comprising the peptides of Formula I, and methods of manufacturing such medicaments.

As used herein, the terms "reducing," "inhibiting," "blocking," "preventing", alleviating," or "relieving" when referring to a compound (e.g., a peptide), mean that the compound brings down the occurrence, severity, size, volume, or associated symptoms of a condition, event, or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, or 100% compared to how the condition, event, or activity would normally exist without application of the compound or a composition comprising the compound. The terms "increasing," "elevating," "enhancing," "upregulating","improving," or "activating" when referring to a compound mean that the compound increases the occurrence or activity of a condition, event, or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, 100%, 150%, 200%, 250%, 300%, 400%, 500%, 750%, or 1000% compared to how the condition, event, or activity would normally exist without application of the compound or a composition comprising the compound.

The following examples are included to demonstrate certain aspects of the invention. It should be appreciated by those of skill in the art that the techniques disclosed in the examples, which represent techniques known to function well in practicing the invention, can be considered to constitute preferred modes for its practice. However, those of skill in the art should, in light of the present disclosure, appreciate that many changes can be made in the specific disclosed embodiments and still obtain a like or similar result without departing from the spirit and scope of the invention. The examples are provided for illustration purposes only and are not intended to be limiting.

EXAMPLE 1

Binding and Activation of Human Opioid Receptors

The peptides of Formula I showed surprisingly high affinity (subnanomolar) for the human mu opioid receptor with selective binding relative to the delta and kappa opioid receptors. The compounds were tested in standard binding assays using $^3$H-DAMGO (tritiated [D-Ala$^2$, N-Me-Phe$^4$, Gly-ol]-enkephalin; CAS #78123-71-4), $^3$H-DPDPE (CAS#88373-73-3), and $^3$H-U69593 (CAS #96744-75-1) to label mu, delta and kappa receptors, respectively, in membranes from CHO cells expressing human cloned receptors. As shown in Table 2, endomorphin-1 (EM1, SEQ ID NO:8) and endomorphin-2 (EM2, SEQ ID NO:9) are the most selective endogenous mu agonists previously reported. Analogs based on these natural opioids show greater affinity for the mu receptor, albeit with less selectivity. Tetrapeptide endomorphin analogs described earlier (U.S. Pat. No. 5,885,958; ck1, Tyr-c[D-Lys-Trp-Phe] (SEQ ID NO:10); ck2, Tyr-c[D-Lys-Phe-Phe] (SEQ ID NO:11)) showed the highest affinity of the compounds tested. Peptides of Formula I, which include a hydrophilic amino acid and amidated carboxy-terminus (Compounds 1, 2, 5) retained high affinity binding, but increased selectivity for the mu receptor.

TABLE 2

Compound binding to opioid receptors.

| | $K_i$ (nM) | | | Selectivity | |
|---|---|---|---|---|---|
| | Mu | Delta | Kappa | Delta/Mu | Kappa/Mu |
| Morphine | 0.92 | 242 | 56 | 264 | 61 |
| DAMGO | 0.78 | 589 | 334 | 754 | 429 |
| EM1 | 2.07 | 1215 | >10000 | 587 | >5000 |

TABLE 2-continued

Compound binding to opioid receptors.

| | $K_i$ (nM) | | | Selectivity | |
|---|---|---|---|---|---|
| | Mu | Delta | Kappa | Delta/Mu | Kappa/Mu |
| EM2 | 1.32 | 5704 | >10000 | 4328 | >5000 |
| ck1 | 0.32 | 28 | 35 | 90 | 111 |
| ck2 | 0.36 | 3 | 12 | 9 | 33 |
| Compound 1 | 0.49 | 132 | 128 | 267 | 260 |
| Compound 2 | 0.73 | 69 | 71 | 94 | 98 |
| Compound 5 | 0.43 | 140 | 29 | 328 | 67 |

Figure 4:
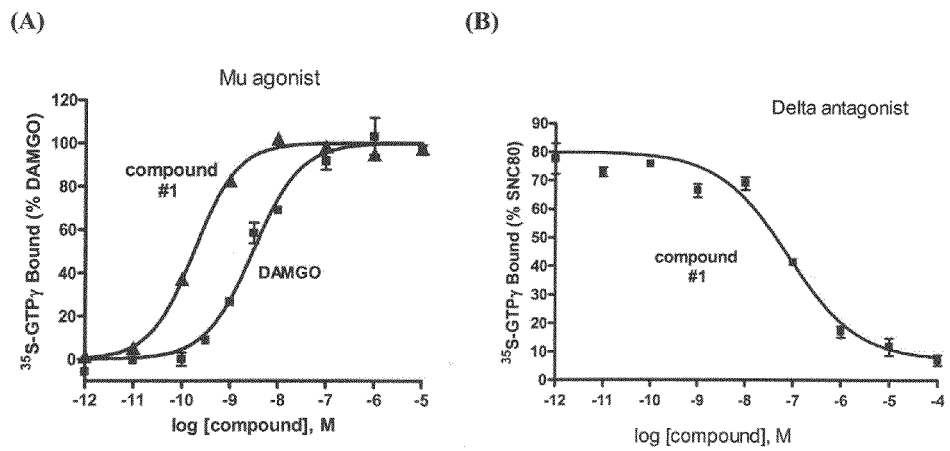
FIG. 4 shows opioid receptor binding activity for Compound 1. (A) mu receptor binding of "Compound 1" (triangles) or DAMGO (squares). (B) Antagonist activity of Compound 1 against binding of SNC80 to delta receptor.

Receptor Activation: GTPγS Functional Assay. Functional activation of the three opioid receptors was tested in standard assays in which the non-hydrolysable GTP analog, $^{35}$S-GT-PγS, was used to quantify activation of cloned human opioid receptors expressed in cell membranes. FIG. 4A shows that Compound 1 is a full efficacy agonist with significantly greater potency than the reference compound, DAMGO. FIG. 4B shows that Compound 1 exhibits unexpected full efficacy as a delta antagonist; i.e., it is able to inhibit the delta activation produced by an $ED_{80}$ dose of the reference delta agonist, SNC80 (CAS #156727-74-1). Table 3 shows that all agonists tested are potent activators of the mu receptor, with $EC_{50}$ (median effective concentration) values at low-nanomolar to sub-nanomolar concentrations. All compounds were found to be full efficacy (>90%) agonists at the mu receptor. The endomorphins and the compounds of Formula I of the invention show remarkable selectivity for receptor activation, with delta activation below 50% at concentrations up to 10 μM, reflecting selectivity >100000. Compounds 1 and 3, however, showed full efficacy delta antagonism; Compound 1 exhibited this antagonism at a relatively low concentration.

TABLE 3

Opioid receptor activation by compounds.

| | Agonist $EC_{50}$ (nM) | | | Selectivity | | Delta Antagonist | |
|---|---|---|---|---|---|---|---|
| | mu | delta | kappa | delta/mu | kappa/mu | IC 50 | efficacy |
| MS$^a$ | 3.90 | 1245 | 2404 | 319 | 616 | | |
| DAMGO | 1.98 | 3641 | 13094 | 1839 | 6613 | | |
| ck1 | 0.21 | 138 | 469.51 | 658 | 2236 | | |
| ck2 | 0.15 | 7 | 206.11 | 44 | 1374 | | |
| EM1 | 1.82 | >100000 | >100000 | >50000 | >50000 | 4287 | 100 |
| EM2 | 8.44 | >100000 | >100000 | >10000 | >10000 | 30000 | 88 |
| Comp. 1 | 0.15 | >100000 | 963.79 | >500000 | 6425 | 105 | 93 |
| Comp. 2 | 0.99 | >100000 | 12114.00 | >100000 | 12236 | 2750 | 51 |
| Comp. 5 | 0.22 | >100000 | 740.34 | >400000 | 3365 | 557 | 100 |

$^a$morphine sulfate

Receptor Activation: Beta-Arrestin Recruitment. Beta-arrestin is an intracellular protein that is recruited to the mu opioid receptor following activation by agonists. It has been shown to activate intracellular signaling pathways that in many cases are independent of well-known G-protein mediated pathways. It has recently been shown that beta-arrestin knockout mice exhibit altered responses to morphine, including increased analgesia and decreased side effects such as tolerance, respiratory depression, and constipation (16). These results indicate that the analgesic and side-effects of morphine are separable by manipulation of cell signaling processes. These findings also provide support for the recent concept known variously as "functional selectivity", "biased agonism","agonist directed signaling" and other descriptions. According to this concept, agonists capable of producing a different cascade of signaling at a given receptor could produce a different profile of desired and undesired effects relative to other agonists for that receptor. Three of the analogs of this invention were tested and showed patterns of beta-arrestin recruitment (ranging from high potency with low efficacy to moderate potency with significant efficacy) that were different from each other and from morphine. Together with the differential analgesic/side-effect profiles relative to morphine described in previous examples, the beta arrestin results suggest that these compounds exhibit "functional selectivity", favoring analgesia over adverse side-effects.

Beyond the value of high mu agonist selectivity (i.e., exclusion of potential side-effects resulting from activation of multiple receptors), delta antagonism is expected to attenuate opioid-induced tolerance, dependence, and reward. As first shown in 1991 (1) and supported in numerous studies since, delta antagonists can reduce morphine-induced tolerance and dependence, while maintaining or enhancing analgesia. Recent studies (11) have also shown reduced rewarding properties of mu agonist/delta antagonists as reflected in the conditioned place preference (CPP) test described below. The activity of the peptides of Formula I (e.g., Compound 1) as mu agonists/delta antagonists as well as at mu/delta receptor dimers indicate that the peptides will produce effective analgesia with reduced tolerance, dependence, and reward (18).

EXAMPLE 2

Providing Analgesia of Greater Duration, but with Reduced Respiratory Depression, Relative to Morphine After Intravenous Administration Respiratory depression is a major safety issue in the use of opioids. An opioid providing analgesia as effective as that produced by morphine, but with less respiratory depression, would be a major advance for the safe use of opioid analgesics. Effectiveness after systemic administration, such as intravenous (i.v.) injection, is unusual for peptide-based compounds, and would be critical for the clinical utility thereof. Two peptides (Compounds 1 and 2) were tested for their effects on respiration (minute ventilation) and duration of antinociception relative to morphine. Rats with indwelling jugular catheters were placed in a BUXCO whole body plethysmograph apparatus for determining multiple respiratory parameters. For 20 minutes following i.v. injection of vehicle (saline), baseline minute ventilation was determined. Animals were then injected with morphine or test compound and changes from baseline were determined for 20 minutes, the period of maximal inhibition of minute ventilation by all compounds. The standard tail-flick (TF) test was used to determine antinociception. A baseline test was conducted before placing the animal in the BUXCO chamber, at the end of the 20-minute respiratory test, and at every 20 minutes thereafter until the TF latency returned to below 2× baseline TF. Baseline latencies were 3-4 seconds and a cut-off time ("maximal antinociception") was set at 9 seconds to avoid tissue damage.

Figure 5:
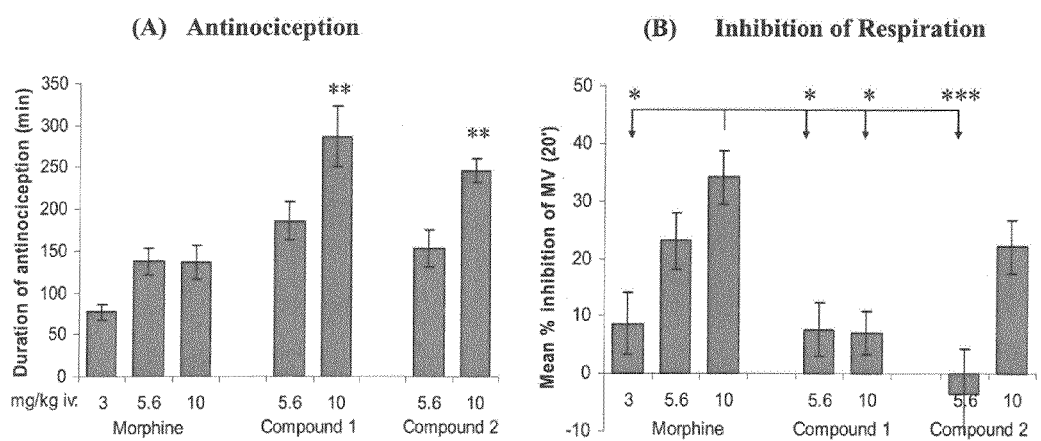
FIG. 5 shows effects of compounds on antinociception and respiration. (A) Effects of Compounds 1 and 2 on antinociception as compared with morphine. **=$p<0.01$. (B) Effects of Compounds 1 and 2 on respiratory minute volume (MV) over a 20-minute period as compared to morphine. *$p<0.05$. ***$p<0.001$.

FIG. 5A shows that 10 mg/kg doses of Compounds 1 and 2 produced significantly longer antinociception than all other treatments (**=p<0.01) and 5.6 mg/kg doses produced antinociception similar to the 10 mg dose of morphine. Despite the greater antinociceptive effect of Compounds 1 and 2, significantly (*p<0.05) less inhibition of respiration was observed in both doses of Compound 1 and in the 5.6 mg/kg dose of Compound 2 (FIG. 5B). These results indicate an unexpected and clearly safer therapeutic profile for the peptides of Formula I over the current standard opioid analgesic.

EXAMPLE 3

Providing Analgesia of Greater Duration than Morphine with Reduced Impairment of Neuromotor Coordination and Cognitive Function Neuromotor and cognitive impairment are characteristics of opioids that are of particular importance in two populations, i.e., military combat troops, where escape from immediate danger can require unimpaired motor and cognitive skills, and the elderly, where these impairments can exacerbate compromised function including impaired balance, which can lead to increased risk of fractures.

EXAMPLE 3a

Neuromotor Coordination

Figure 6:
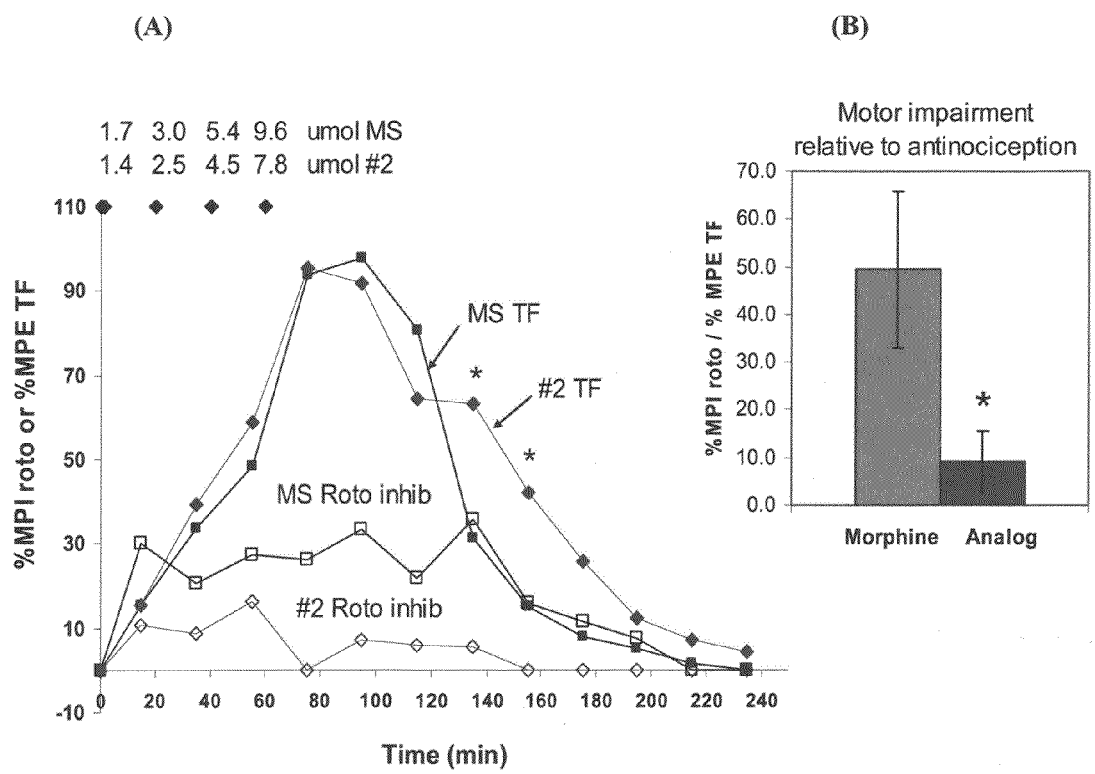
FIG. 6 shows the effects of Compound 2 on antinociception and motor impairment. (A) The effects of Compound 2 (filled triangles) and morphine sulfate (MS, filled squares) on antinociception were measured by the tail flick (TF) test. Also, the effects of Compound 2 (open triangles) and morphine sulfate (open squares) on motor behavior were measured. (*=$p<0.05$). (B) The bar graph shows the ratio of the area under the curve (AUC) for percent motor impairment relative to the AUC for percent antinociception. This ratio is significantly greater (*p<0.05) for morphine than for Compound 2, consistent with greater motor impairment relative to analgesia for morphine.

FIG. 6A illustrates that Compound 2 produces significantly greater antinociception, but significantly reduced motor impairment, relative to morphine (MS). Both compounds were administered by cumulative intravenous (i.v.) doses in rats. Increasing quarter-log doses were given every 20 minutes, and a tail flick (TF) test (a test of latency to remove the tail from a hot light beam) followed by a rotorod test were conducted about 15 minutes after each injection. Escalating doses were given until each animal showed greater than 90% maximum possible effect (% MPE) on the TF test, determined as: [(latency to TF minus baseline latency)/(9 sec maximum (cut off) time to avoid tissue damage) minus baseline)]×100. The animal was then placed on a rod that rotated at speeds escalating to 13 revolutions per minute (RPM) over 3 minutes, and the latency to fall from the rod was determined. Only animals that consistently remained on the rod for the full 180 seconds during training in the drug-naïve state were tested. % Maximum Possible Inhibition (%MPI) of motor coordination was determined as 100−(latency to fall/180× 100).

The two compounds showed similar onset to maximal antinociception, but Compound 2 produced significantly longer antinociception, as reflected by TF latencies significantly (*=p<0.05) longer than those of the morphine group at 135 and 155 minutes (FIG. 6A). Despite this greater antinociception, the motor impairment was significantly less than that of morphine (FIG. 6B, *p<0.05). The impairment of motor behavior by morphine was significantly above that of vehicle controls (*p<0.05) while that of Compound 2 was not.

EXAMPLE 3b

Cognitive Impairment

A widely used standard test of cognitive function is the Morris Water Maze (MWM). During training, rats learn to find a hidden escape platform based on spatial memory. Average latency to the platform, as well as average distance from the platform (a measure unaffected by swim speed), decrease as the task is acquired and provide indices of spatial memory. After 4 days of training, an injection of morphine produced impairment of spatial memory, as reflected by a significant increase in the latency to, and average distance from, the platform. By contrast, Compound 2, at doses that provide equal or greater antinociception than morphine, did not produce significant impairment. These results indicate an unexpected and superior therapeutic profile of the peptides of Formula I with regard to cognitive function relative to the current standard opioid analgesic.

EXAMPLE 4

Providing Analgesia of Greater Duration, but Reduced Reward, Relative to Morphine Opioids remain the standard treatment for relief of severe pain, but diversion of pain medications for non-pain use has become a serious national problem (see U.S. Department of Health and Human Services Substance Abuse and Mental Health Services Administration, found at world wide website oas.samhsa.gov/2k9/painRelievers/ nonmedicalTrends.pdf). Considerable efforts in academia and industry have focused on "tamper-proof" versions of opioid medications, but there has been little success in developing opioids that provide highly effective analgesia with minimal abuse potential. The conditioned place preference (CPP) paradigm is a widely accepted model for demonstrating rewarding properties of drugs, and all major classes of abused drugs produce CPP, including opioids such as morphine and heroin. Briefly, animals are first allowed, on Day 1, to freely explore a 3-compartment apparatus consisting of a small "start box" and two larger compartments that are perceptually distinct (gray vs. black and white stripes in this example). For the next three days, the animals are given an i.v. injection of drug and confined to one compartment, and vehicle is given in the other. The time at which the drug or vehicle is given (a.m. or p.m.) is counterbalanced, as is the compartment in which the drug is given (preferred or non-preferred, as determined during the baseline test). This unbiased design allows for detection of both drug preference and drug aversion. After three days of conditioning (Days 2, 3 and 4), the animal is allowed free access to all compartments on Day 5 in the drug-free state and the change in absolute time and proportion of time spent in the drug-paired compartment are determined. A significant increase in the time or proportion of time spent in the drug-paired compartment on the post-conditioning test day relative to that on the pre-conditioning baseline test is interpreted as a conditioned place preference, reflective of rewarding properties and potential abuse liability.

Figure 7:
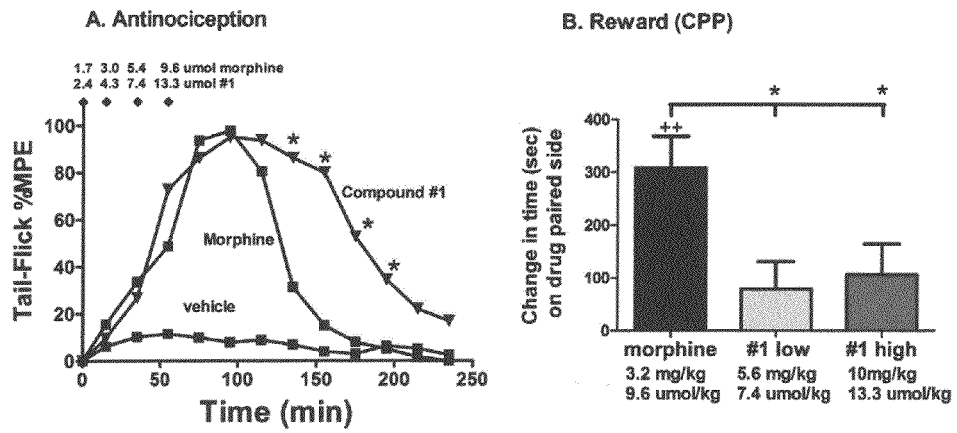
FIG. 7 shows the effects of compounds on drug abuse liability. (A) The effects of Compound 1 (filled triangles), morphine (filled squares), and vehicle (filled circles) on antinociception were measured by the tail flick (TF) test.

When the cumulative doses of either morphine or Compound 1 that were shown to produce maximal antinociception (FIG. 7A) were tested for the ability to induce CPP (FIG. 7B), morphine produced a significant (*** $p<0.01$) increase in the time spent on the drug side, while Compound 1 did not, even though significantly (* $p<0.05$) greater antinociception (FIG. 7A) was observed with Compound 1 from about 140 to 180 minutes after its injection. Compounds 2 and 5 also showed no significant CPP at doses producing antinociception equal to those of morphine that produced CPP. In a complementary paradigm in which rats were provided access to morphine or EM analogs for self-administration, access to morphine, but not analogs, resulted in significant self-administration. These findings are consistent with less abuse liability for the novel analogs relative to morphine.

EXAMPLE 5

Alleviation of Chronic Pain

Chronic pain affects a large proportion of the population. One form of chronic pain, neuropathic pain, is particularly difficult to treat. FIG. 8 shows that Compounds 1, 2 and 5 provide unexpectedly potent relief of neuropathic pain induced by the spared nerve injury (SNI) model in the rat. As demonstrated in FIG. 8A, prior to SNI surgery ("pre-surgery"), an average pressure of about 177 g applied to the hindpaw with a Randall-Selitto device was required to elicit a paw withdrawal response. About 7 to 10 days post-surgery, the animals showed hyperalgesia, indicated by a reduction in the average pressure (to about 70 g) required to elicit withdrawal. Drugs were administered as intrathecal cumulative doses chosen to produce full alleviation of the hyperalgesia. Times at which the reversal was significantly ($p<0.05$ to $0.001$) above vehicle are shown in bars at the top. Compound 5 showed similar reversal times (about 80 min), and Compounds 1 and 2 showed significantly longer reversal times (about 120 and 260 min, respectively) relative to morphine (about 80 min). Scores for Compound 1 were also significantly above those of morphine from 155-215 min (dashed bar). Dose-response curves (FIG. 8B) showed that all three analogs are significantly more potent than morphine, as determined by the dose required to fully (100%) reverse the hyperalgesia, i.e., return to the pre-surgical baseline response (pre-surgical minus post surgical pressure). Compounds 1, 2, and 5 reversed mechanical hypersensitivity at doses about 80-fold to 100-fold lower than morphine (about 0.01 to 0.014 µg compared to about 1.14 µg for morphine). On a molar basis, this represents about 180 to 240 fold greater potency than morphine against neuropathic pain. Similar results were observed after other forms of chronic pain including post-incisional (post-operative) and inflammatory pain induced by Complete Freund's Adjuvant (CFA). The foregoing examples are illustrative, but not exhaustive, as to the types of acute or chronic pain for which the peptides of Formula I are effective.

EXAMPLE 6

Reduced Tolerance and Glial Activation Relative to Morphine

A major limiting factor for the usefulness of opioid medications is tolerance, which requires increasing doses to maintain an analgesic effect. Reduction of the potential for tolerance would be a very important advantage for a novel analgesic. In addition, several recent studies have shown that repeated opioid exposure sometimes leads to "paradoxical" opioid-induced pain. Increased responsiveness to normally noxious stimuli (hyperalgesia) or normally non-noxious stimuli such as touch (allodynia) have been reported. Explanations for the tolerance and opioid induced hypersensitivity include the possibility that activation of glia, a reflection of an inflammatory response, results in an increased release of substances that activate or sensitize neuronal transmission of nociceptive signals. Specifically, enhanced release of "pronociceptive" cytokines and chemokines are thought to mediate the enhanced pain sensitivity sometimes observed after chronic exposure to opioids. In addition, several studies have linked this phenomenon to opioid tolerance based on the concept that increasing doses of opioids are required to overcome the increased pronociceptive effects of the released compounds. Described below are the unexpected findings that: (1) Compounds 1, 2 and 5 produce significantly less tolerance relative than morphine, and (2) that in direct comparison to morphine, and in contrast to morphine and most clinically used opioids, the analogs do not induce an inflammatory glial activation response after chronic administration. In addition to their potential value for reduced escalation of doses required during chronic administration, the analogs of Formula I could be ideal for opioid rotation and for a wide range of situations where ongoing inflammatory conditions may be exacerbated by treatment with morphine. This approach would also be superior to use of an anti-inflammatory agent as an adjuvant to opioid treatment.

Compounds 1, 2 and 5 all showed greater potency, reduced tolerance and reduced glial activation relative to morphine. For simplicity, only Compound 2 is shown in comparison to morphine in FIG. 9. The experiment was designed to model clinical use of opioids by titrating to full antinociception in each subject, and maintaining steady blood levels, in this case through use of osmotic minipumps. Doses producing matched initial antinociception were determined for morphine and analog by intrathecal injection of the cumulative dosing paradigm described above for the rotorod and neuropathic pain models. Doses were increased until each rat achieved full antinociception (100% MPE). The $ED_{50}$ for all compounds in opioid naïve animals was determined and Compound 2 was found to be over 20-fold more potent ($p<0.001$) than morphine ($ED_{50}$=0.01 µg±0.001 compared to 0.253 µg±0.05 for morphine, n=5-7). This translates on a molar basis to about 40-fold greater potency for the analog. Immediately after the first test, ALZET osmotic minipumps (Durect Corp, Cupertino, Calif.) were implanted subcutaneously and connected to the intrathecal catheter. The primed pumps delivered morphine or analog at 2 µg/hr or 0.056 µg/hr for about 7 days, respectively. The 2 µg/hr morphine dose was chosen based on previous studies in which this dose was shown to produce glial activation in the dorsal horn in a similar paradigm (Tawfik et al., 2005). The dose of analog was chosen using a similar ratio to the $ED_{50}$ (about 7× to 8×). A second cumulative dose-response curve was generated on Day 7 after minipump implantation to determine the shift in $ED_{50}$ as an index of relative tolerance. As shown in FIG. 9, the $ED_{50}$ of morphine shifted to 16±3.3 µg (over 60-fold) while that of compound 2 shifted only about 8.5 fold to about 0.11±0.02 µg. Compounds 1 and 5 showed similar results with potencies over 20× greater than morphine and shifts less than 20 fold. These results show that EM analogs cause unexpected and significantly less tolerance than morphine.

As shown in FIG. 10, morphine produced significant glial activation, but for all 3 analogs, activation was not significantly different from vehicle and was significantly less than morphine, establishing differential glial effects for morphine compared to EM analogs (Compounds, 1, 2, and 5). Rats used in the above tolerance experiment were perfused after the final behavioral test and analyzed for glial activation as indicated by (A) GFAP staining for astroglia and (B) phospho-p38, a signaling pathway activated in microglia by morphine. Five sections from each of 5-7 animals/group were analyzed for integrated density of staining with the IMAGE J program. Morphine, but none of the analogs, showed significantly greater induction than vehicle. Values for all analogs were significantly below those of morphine (*,,*=$p<0.05$, 0.01,0.001, respectively, compared to indicated groups). These data provide evidence that, at doses producing equal or greater antinociception, the analogs produce unexpectedly less glial activation and this is associated with reduced tolerance.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

The following references are referred to in this application and are incorporated herein by reference in their entirety:

(1) Abdelhamid E. E., Sultana M., Portoghese P. S. and Takemori A. E. (1991) Selective blockage of delta opioid receptors prevents the development of morphine tolerance and dependence in mice. *J. Pharmacol. Exp. Ther.* 258, 299-303;

(2) Bodanszky M. (1993) *Peptide Chemistry: A Practical Textbook*. Springer-Verlag, New York;

(3) Chen Y., Mestek A., Liu J., Hurley J. A. and Yu L. (1993) Molecular cloning and functional expression of a µ-opioid receptor from rat brain. *Mol. Pharmacol.* 44, 8-12;

(4) Czapla M. A., Gozal D., Alea O. A., Beckerman R. C. and Zadina J. E. (2000) Differential cardiorespiratory effects of endomorphin 1, endomorphin 2, DAMGO, and morphine. *Am. J. Respir. Crit Care Med* 162, 994-999;

(5) Czapla M. A. and Zadina J. E. (2005) Reduced suppression of $CO_2$-induced ventilatory stimulation by endomorphins relative to morphine. *Brain Res.* 1059, 159-166;

(6) Evans C. J., Keith D. E., Jr., Morrison H., Magendzo K. and Edwards R. H. (1992) Cloning of a delta opioid receptor by functional expression. *Science* 258, 1952-1955;

(7) Gianni W., Ceci M., Bustacchini S , Corsonello A., Abbatecola A. M., Brancati A. M., Assisi A., Scuteri A., Cipriani L. and Lattanzio F. (2009) Opioids for the treatment of chronic non-cancer pain in older people. *Drugs Aging* 26 Suppl 1, 63-73;

(8) Kieffer B. L. (1999) Opioids: first lessons from knock-out mice. *Trends Pharmacol. Sci* 20, 19-26;

(9) Kieffer B. L., Befort K., Gaveriaux-Ruff C. and Hirth C. G. (1992) The δ-opioid receptor: isolation of a cDNA by expression cloning and pharmacological characterization. *Proc. Natl. Acad. Sci USA* 89, 12048-12052;

(10) Kuehn B. M. (2009) New pain guideline for older patients: avoid NSAIDs, consider opioids. *JAMA* 302, 19;

(11) Lenard N. R., Daniels D. J., Portoghese P. S. and Roerig S. C. (2007) Absence of conditioned place preference or reinstatement with bivalent ligands containing mu-opioid receptor agonist and delta-opioid receptor antagonist pharmacophores. *Eur. J. Pharmacol.* 566, 75-82;

(12) Meng F., Xie G. X., Thompson R. C., Mansour A., Goldstein A., Watson S. J. and Akil H. (1993) Cloning and pharmacological characterization of a rat K opioid receptor. *Proc. Natl. Acad. Sci USA* 90, 9954-9958;

(13) Minami M., Toya T., Katao Y., Maekawa K., Nakamura S., Onogi T., Kaneko S. and Satoh M. (1993) Cloning and expression of a cDNA for the rat K-opioid receptor. *FEBS Lett.* 329, 291-295;

(14) Nishi M., Takeshima H., Fukuda K., Kato S. and Mori K. (1993) cDNA cloning and pharmacological characterization of an opioid receptor with high affinities for K-subtype-selective ligands. *FEBS Lett.* 330, 77-80;

(15) Prokai-Tatrai K., Prokai L. and Bodor N. (1996) Brain-targeted delivery of a leucine-enkephalin analogue by retrometabolic design. *J. Med Chem.* 39, 4775-4782;

(16) Raehal, KM, JKL Walker, and LM Bohn (2005) Morphine Side Effects in β-Arrestin 2 Knockout Mice. *J. Pharmacol. Exp. Ther.* 314, 1195-1201

(17) Rozenfeld R. and Devi L. A. (2010) Receptor heteromerization and drug discovery. *Trends Pharmacol. Sci* 31, 124-130;

(18) Stewart J. M. and Young J. D. (1984) *Solid Phase Peptide Synthesis*. Pierce Chemical Company;

(19) Tawfik V. L., LaCroix-Fralish M. L., Nutile-McMenemy N., DeLeo J. A. (2005) Transcriptional and translational regulation of glial activation by morphine in a rodent model of neuropathic pain. *J. Pharmacol. Exp. Ther.* 313,1239-1247;

(20) Thompson R. C., Mansour A., Akil H. and Watson S. J. (1993) Cloning and pharmacological characterization of a rat μ opioid receptor. *Neuron* 11, 903-913;

(21) Wang J. B., Johnson P. S., Persico A. M., Hawkins A. L., Griffin C. A. and Uhl G. R. (1994) Human μ opiate receptor. cDNA and genomic clones, pharmacologic characterization and chromosomal assignment. *FEBS Lett.* 338, 217-222;

(22) Wilson A. M., Soignier R. D., Zadina J. E., Kastin A. J., Nores W. L., Olson R. D. and Olson G. A. (2000) Dissociation of analgesic and rewarding effects of endomorphin-1 in rats. *Peptides* 21, 1871-1874; and (23) Zadina J. E., Hackler L., Ge L. J. and Kastin A. J. (1997) A potent and selective endogenous agonist for the μ-opiate receptor. *Nature* 386, 499-502.

What is claimed is:

1. A cyclic peptide wherein the peptide consists of the amino acid sequence of Tyr-c[D-Lys-Trp-Phe-Glu]-NH$_2$ (SEQ ID NO:1) or wherein the peptide consists of the amino acid sequence of Tyr-c[D-Lys-Trp-Phe-Asp]-NH$_2$ (SEQ ID NO:5).

2. A pharmaceutical composition comprising a pharmaceutically acceptable carrier and the peptide of claim 1.

3. A method of treating pain comprising administering to a subject in need thereof an analgesic amount of the peptide of claim 1.

4. The method of claim 3, further comprising administering an opioid drug to the subject.

5. The method of claim 4, wherein the steps of administering the peptide and the opioid drug are performed concurrently.

6. The method of claim 4, wherein the steps of administering the peptide and the opioid drug are performed alternately on a rotating basis.

7. The method of claim 3, wherein the step of administering the peptide is performed by administering repeated, increasing doses of the peptide to the subject until full antinociception is achieved, and then maintaining the blood level of the peptide at the level obtained at full antinociception.

8. The method of claim 3, wherein the peptide is administered parenterally.

* * * * *

UNITED STATES PATENT AND TRADEMARK OFFICE
CERTIFICATE OF CORRECTION

PATENT NO. : 8,716,436 B2  Page 1 of 1
APPLICATION NO. : 13/477423
DATED : May 6, 2014
INVENTOR(S) : James E. Zadina et al.

It is certified that error appears in the above-identified patent and that said Letters Patent is hereby corrected as shown below:

IN THE SPECIFICATION

Column 6, line 67, after the word "alanine" insert --.--.

Column 7, line 4, delete "a-amino acid" and insert --α-amino acid--.

line 15, delete "a-amino acid" and insert --α-amino acid--.

line 15, after the word "phenylalanine" insert --.--.

line 16, delete "$X_i$" and insert --$X_1$--.

line 31, after the word "endomorphins" insert --.--.

Signed and Sealed this
Thirteenth Day of January, 2015

Michelle K. Lee
*Deputy Director of the United States Patent and Trademark Office*